United States Patent [19]
Witt

[11] 3,950,448
[45] Apr. 13, 1976

[54] DETERGENT-GRADE ALKYLATE PRODUCTION

[75] Inventor: Paul A. Witt, Arlington Heights, Ill.

[73] Assignee: Universal Oil Products Company, Des Plaines, Ill.

[22] Filed: Feb. 24, 1975

[21] Appl. No.: 552,016

[52] U.S. Cl. ..... 260/671 B; 260/671 R; 260/674 R; 260/674 A
[51] Int. Cl.² ............... C07C 3/54; C07C 7/04
[58] Field of Search ........ 260/671 R, 671 B, 674 R, 260/674 A

[56] References Cited
UNITED STATES PATENTS

| | | | |
|---|---|---|---|
| 2,851,503 | 9/1958 | Shiffler | 260/671 |
| 3,408,264 | 10/1968 | Ward | 260/674 |
| 3,483,265 | 12/1969 | Rakestraw et al. | 260/671 |
| 3,484,498 | 12/1969 | Berg | 260/671 |
| 3,494,971 | 2/1970 | Fenske | 260/671 |

Primary Examiner—Delbert E. Gantz
Assistant Examiner—C. E. Spresser
Attorney, Agent, or Firm—James R. Hoatson, Jr.; Robert W. Erickson; William H. Page, II

[57] ABSTRACT

Detergent-grade alkylate is produced by the HF-acid catalyzed reaction of aromatic hydrocarbons and an olefinic hydrocarbon. The process utilizes a unique fractionation facility for the recovery and use of an aromatic concentrate, and ultimate recovery of the detergent alkylate product. Integrated within the process is a combination stripping/fractionation column having a contact-condenser disposed therein.

10 Claims, 1 Drawing Figure

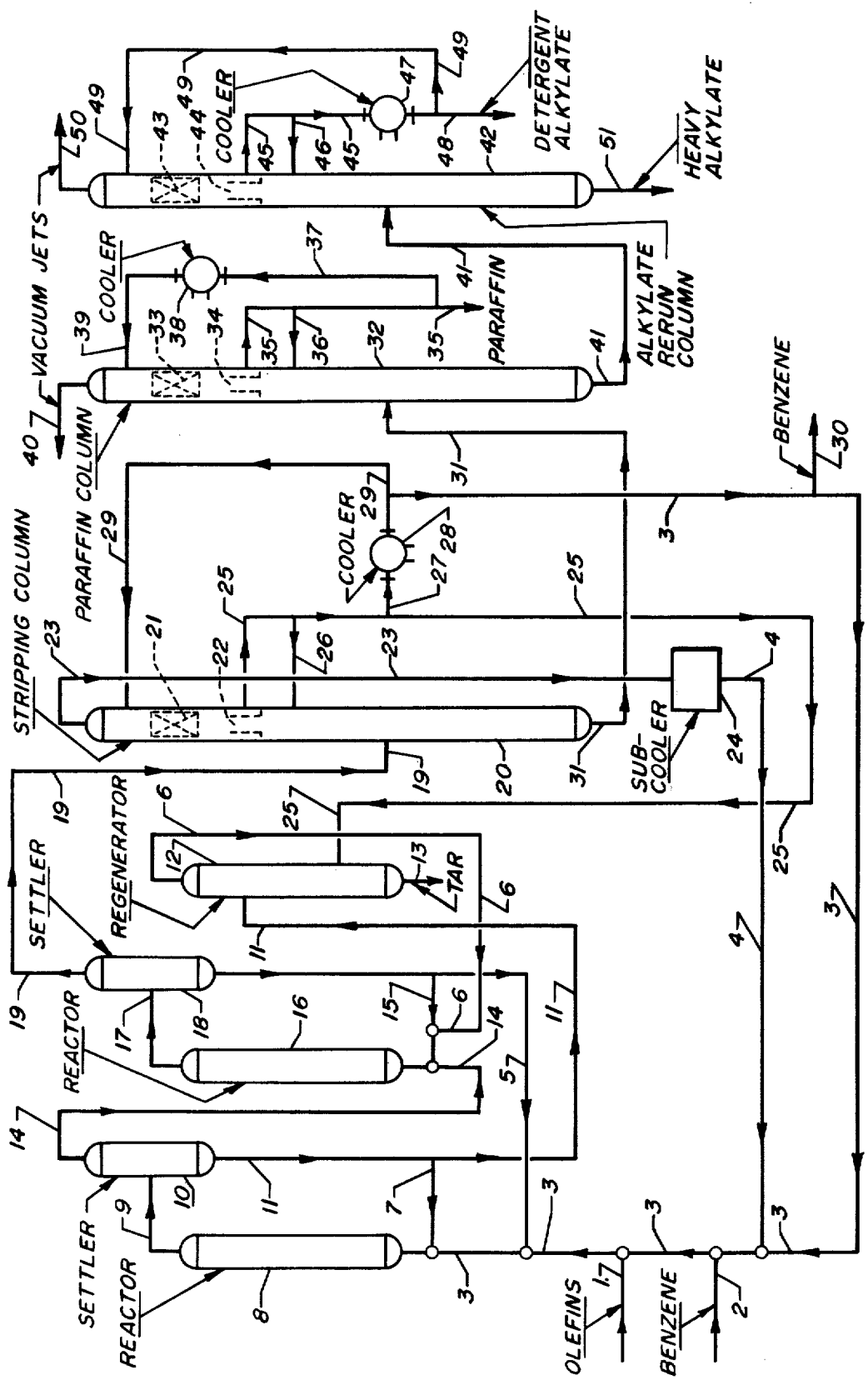

DETERGENT-GRADE ALKYLATE PRODUCTION

APPLICABILITY OF INVENTION

The process encompassed by the present inventive concept is intended for use in the preparation of detergent-grade alkylate, and is applicable to both "soft" detergent and "hard" detergent. These terms, soft and hard, have become synonymous, in the appropriate art, with "biodegradable" and "non-biodegradable", respectively. This distinction stems primarily from the type of olefinic hydrocarbon, containing from about six to about twenty carbon atoms per molecule, and most generally from about ten to about fifteen carbon atoms per molecule, employed in the manufacturing process. Two principal olefin sources exist: one constitutes the product resulting from the polymerization of propylene-rich streams which may contain varying quantities of butenes, commonly referred to as "tetramer". Prior art indicates knowledge that the alkylaryl sulfonates, or alkylaryl amines, resulting from the detergent alkylate produced from an aromatic hydrocarbon and tetramer olefins, is substantially non-biodegradable, or of the "hard" variety. This is due primarily to the branched-chain character of the alkane substituent.

Relatively recently, a dehydrogenation process has been announced which produces the most desirable olefinic hydrocarbon -- i.e. straight-chain mono-olefins -- from normal paraffins of the desired carbon number. The sulfonated, or nitrated detergents prepared from this type of alkylate are biodegradable by sewage bacteria and are, therefore, of the "soft" variety. Biodegradability is determined by the arylalkane hydrocarbon employed in the preparation of the detergent, with the degree thereof being increased as branching of the alkane substituent is decreased. In particular, the art acknowledges that the most readily biodegradable detergents stem from arylalkanes where the long-chain alkyl group is of the normal, straight-chain configuration. Consequently, an increasing demand for this type of hydrocarbon has developed. Since these are customarily prepared by the alkylation route, they have come to be commonly referred to as "linear detergent alkylate".

Briefly, the linear detergent alkylate can be converted to a wide variety of detergents through a likewise wide variety of techniques. Detergent alkylate may be sulfonated, and thereafter neutralized with a suitable alkaline base to form an alkylaryl sulfonate (anionic) most often used as a household detergent. The detergent alkylate may be converted to a non-ionic type detergent through nitration to form a nuclearly mono-nitrated intermediate which, upon subsequent reduction, yields the corresponding alkylaryl amine. The amino radical is thereafter reacted with an alkylene oxide to form an alkylaryl-polyoxyalkylated amine which is also a highly effective detergent.

As described herein, the present process is applicable for the production of detergent-grade alkylate of both the soft and hard varieties. Stress is placed on the linear detergent alkylate (soft) in view of its preference within the detergent art respecting the degree of biodegradability. It is understood that the intent is not to so limit the present invention, the scope and spirit of which is defined by the appended claims.

OBJECTS AND EMBODIMENTS

A principle object of my invention is to provide a technique for recovering unreacted aromatic hydrocarbons and HF from the alkylation product effluent. A corollary objective resides in providing a stream to be used as the stripping medium in the acid-regenerator generally integrated into an HF-acid alkylation unit.

Specifically, an objective of the invention herein described is to afford distinct improvements in a process for preparing linear detergent alkylate from mono-olefins, having from about ten to about fifteen carbon atoms per molecule, and benzene.

Therefore, one embodiment of my invention is directed toward a process for the production of an alkyl-aromatic hydrocarbon which comprises the steps of: (a) reacting aromatic hydrocarbons with an olefinic hydrocarbon in contact with a hydrogen fluoride catalyst, in a reaction zone at alkylation conditions selected to produce alkylated aromatics; (b) separating the resulting reaction zone effluent, in a separation zone, to provide a hydrocarbon-rich stream, containing hydrogen fluoride, and a hydrogen fluoride-rich stream; (c) introducing at least a portion of said hydrogen fluoride-rich stream into a regeneration zone to produce regenerated hydrogen fluoride and recycling regenerated hydrogen fluoride to said reaction zone; (d) introducing said hydrocarbon-rich stream, containing aromatic hydrocarbons, HF, alkylaromatics, polyalkyl aromatics, and/or polyaryl alkanes, into a combination stripping/fractionation zone having a contact-condenser disposed therein, and recovering therefrom (i) an overhead fraction rich in aromatic hydrocarbons and HF, (ii) a bottoms fraction containing alkylaromatics, polyalkyl aromatics and/or polyaryl alkanes and (iii) a side-cut fraction containing aromatic hydrocarbons and substantially free from HF; (e) introducing a first portion of said side-cut fraction, at substantially the same temperature, into said column; (f) introducing a second portion of said side-cut fraction into said regeneration zone and countercurrently contacting therein said hydrogen fluoride-rich stream; and, (g) recovering said linear alkylaromatics from said bottoms fraction.

In another embodiment, the present invention is directed toward a method for recovering HF and benzene from a mixture thereof with alkylbenzenes, the alkyl group of which contains from about ten to about fifteen carbon atoms per molecule, polyalkyl benzenes and/or polyphenyl alkanes, which method comprises the steps of: (a) introducing said mixture into a combination stripping/fractionating column, at an intermediate first locus thereof; (b) withdrawing a bottoms fraction from said column, at a lower second locus thereof, containing alkylbenzenes, polyalkyl benzenes, and/or polyphenyl alkanes, substantially free from HF and benzene; (c) withdrawing a side-cut fraction from said column, substantially free from HF, at an intermediate third locus thereof, said third locus being above said first locus and below a contact-condenser disposed in an upper section of said column; (d) introducing a first portion of said side-cut fraction, at substantially the same temperature, into said column, at a fourth locus intermediate said first locus and said third locus; (e) cooling a second portion of the side-cut fraction and introducing said second portion into said column at a fifth locus above said contact-condenser; and, (f) withdrawing HF and benzene as an overhead fraction from said column, through a sixth locus above said fifth locus.

Also afforded is an improved process for producing detergent-grade alkylate which comprises the steps of: (a) reacting aromatic hydrocarbons with an olefinic hydrocarbon in contact with an HF catalyst, in a first reaction zone, at alkylation conditions selected to produce alkylated aromatics; (b) introducing the resulting first reaction zone effluent into a first separation zone to provide a first hydrocarbon phase and a first HF-acid phase; (c) further reacting said first hydrocarbon phase in contact with HF-acid catalyst, in a second reaction zone, at alkylation conditions selected to produce additional alkylated aromatics; (d) recycling a first portion of said first HF-acid phase to said first reaction zone, and introducing a second portion into an upper section of a regeneration zone and countercurrently contacting said second portion therein with an aromatic hydrocarbon-containing stream to provide a regenerated HF-acid phase; (e) recycling at least a portion of said regenerated HF-acid phase to said second reaction zone; (f) introducing the resulting second reaction zone effluent into a second separation zone to provide a second HF-acid phase and a second hydrocarbon phase; (g) recycling at least a portion of said second HF-acid phase to said first reaction zone; (h) introducing said second hydrocarbon phase, containing HF, aromatic hydrocarbons, alkylated aromatics, polyalkyl aromatics and/or polyaryl alkanes into a combination stripping/fractionation zone having a contact-condenser disposed therein, and withdrawing therefrom a side-cut fraction principally containing aromatic hydrocarbons; (i) introducing at least a portion of said side-cut fraction into a lower section of said regeneration zone to countercurrently contact therein the second portion of said HF-acid phase as said aromatic hydrocarbon-containing stream; and, (j) recovering said detergent-grade alkylate from the remainder of said second hydrocarbon phase.

Other objects and embodiments of the process encompassed by my inventive concept will become evident from the following additional description thereof. Such other embodiments are principally directed toward various process operating conditions and techniques. In one such other embodiment, the mole ratio of that portion of the side-cut fraction, to the vaporous material passing into the contact-condenser disposed within the combination stripping/fractionation zone is in the range of about 1.5:1.0 to about 6.0:1.0.

PRIOR ART

It necessarily must be recognized that the prior art is replete with a wide variety of publications; inclusive of issued patents, directed toward the acid-catalyzed alkylation of two dissimilar hydrocarbons. This is especially the situation involving hydrogen fluoride alkylation of an isoparaffin with an olefin, to produce a motor fuel alkylate, which traces its development over an approximately thirty-five year period. Similarly, the HF-acid catalyzed alkylation of an aromatic hydracarbon with an olefinic hydrocarbon is a process having about a thirty year history in petroleum technology. Any attempt herein to delineate exhaustively the entire body of hydrogen fluoride alkylation art would be an exercise in futility. However, it is believed that a brief discussion of two relatively recent United States Patents, in the area of detergent alkylation, is warranted.

U.S. Pat. No. 3,484,498 (Cl. 260-671) discloses a combination process involving (1) dehydrogenation of long-chain normal paraffins to produce mono-olefins, followed by (2) HF-acid catalyzed alkylation of the olefins with a mono-cyclic aromatic hydrocarbon. The preferred alkylatable mono-cyclic aromatic hydrocarbon is benzene, while the preferred normal paraffinic charge to the dehydrogenation zone comprises a mixture of $C_{10}$ to $C_{15}$ paraffins. Product effluent from the dehydrogenation zone, containing unreacted paraffins and the mono-olefins resulting from the conversion of up to about 20.0% of the paraffin feed is, following the removal of hydrogen and light hydrocarbons, introduced into the alkylation system. The fractionation facility recovers the linear detergent alkylate and unreacted normal paraffins which are recycled to the dehydrogenation zone. In one of its embodiments, the present invention utilizes, as charge to the alkylation reaction zone, the mono-olefinic stream from a dehydrogenation unit, including the normal paraffins therein. The latter are separately recovered and removed from the process. Here, however, the similarity ends; there is no indicated recognition of the present novel fractionation facility utilizing the combination stripping/fractionation column which incorporates therein a contact-condenser. This patent does, however, present a fairly complete and comprehensive analysis of the distinction between non-biodegradable and biodegradable detergents, and the practical necessity for the latter type.

U.S. Pat. No. 3,494,971 (Cl. 260-671) is illustrative of the production of soft detergent alkylate using a two-reactor, two-separation zone system as is preferred for the present process. Included is an acid regenerator wherein regenerated acid is recovered via hydrocarbon stripping; however, there is no indication of the source of the hydrocarbon utilized as the stripping medium. Further, there is no recognition of introducing the hydrocarbon phase from the second separation zone into a combination stripping/fractionation column, containing a contact-condenser, and from which substantially pure hydrocarbons are introduced into the acid regenerator.

SUMMARY OF INVENTION

Detergent alkylate is formed by the reaction of an aromatic hydrocarbon and an olefinic hydrocarbon containing from about six to about twenty carbon atoms per molecule. Experience within the detergent industry dictates that the preferred olefins contain from ten to about fifteen carbon atoms per molecule. As hereinbefore stated, there now exist two principal sources of olefinic hydrocarbons; (1) a polymerization (catalytic condensation) process charging propylene and butylenes, and, (2) a dehydrogenation process charging the paraffinic analogs of the desired olefins. The produce from the former is commonly referred to as "tetramer", and results in "hard" detergent when alkylated with an aromatic hydrocarbon. Dehydrogenation enjoys the advantage since it is capable of producing a long-chain mono-olefin from the normal paraffin counterpart. The mono-olefin results in linear alkylate detergent, or "soft", when alkylated with an aromatic hydrocarbon. Suitable aromatic hydrocarbons include benzene, toluene, the xylenes, ethylbenzene, methylethylbenzene, diethylbenzene and mixtures thereof. Since the degree of biodegradability is determined by the degree of branching of the alkyl substituent and, to some extent by the number of alkyl substituents, benzene is the preferred aromatic hydrocarbon. In the interest of brevity, therefore, the following discussion will be directed primarily toward the alkylation of benzene with mono-olefinic hydrocarbons to produce a linear alkylbenzene. This is not intended, however, to so limit my invention.

The alkylation reaction zone, or zones, will be maintained at pressures in the range of about 15 psig. to about 600 psig. and a temperature from 0° F. to about 200° F. Particularly preferred temperatures range from 30° F. to about 120° F. The reactant stream is maintained within the reaction zones for a residence time of about 5 to about 25 minutes. The ratio (volumes) of hydrogen fluoride acid to hydrocarbon is generally in the range of about 0.2:1.0 to about 10.0:1.0, and typically about 2.0:1.0. In order to maximize the yield of the desired alkylbenzene, the mole ratio of benzene, or other aromatic hydrocarbon, to olefinic hydrocarbons is preferably greater than 1.0:1.0. Generally, commercially designed units function at a benzene/olefin ratio from 2.0:1.0 to about 15.0:1.0. The acidity of the HF-acid catalyst within the reaction zones is maintained above about 85.0% -- i.e. from about 86.0% to about 94.0% -- through the use of an acid regenerator which accepts a drag stream from the HF-acid circulation system within the reaction section of the process. The operation of the acid regenerator is such that alkylfluorides are decomposed and a bottoms stream of tar is removed prior to recycling regenerated acid to the reaction zone. In accordance with one embodiment of the present invention, the stripping medium is concentrated benzene recovered from the fractionation section of the process.

The reaction zone effluent is introduced into a settling zone which effects separation thereof into a hydrocarbon phase and an HF-acid phase. Considering only the reaction section of the overall process, including the acid regenerator, in which section two reaction zones are preferably employed, the product effluent from the first reaction zone is introduced into a first separation zone, or acid settler, which provides a first hydrocarbon-rich phase, containing HF-acid, and a first settled HF-acid phase. The hydrocarbon phase is introduced into the second reaction zone. A portion of the HF-acid phase is recycled to the first reaction zone, while a second portion, or drag stream, is introduced into the acid regenerator wherein it is countercurrently contacted with a benzene stream, the source of which is hereinafter set forth. The regenerated acid phase is recycled to the second reaction zone. The effluent from the latter is passed into a second acid settler, the settler acid phase from which is introduced into the first reaction zone. In one embodiment, a portion of the second settled acid phase will be recycled to the second reaction zone. The second hydrocarbon phase, containing HF-acid, is introduced into the fractionation section of the process.

When producing detergent alkylate from tetramer olefins, the feed to the fractionation section of the process contains unreacted benzene, HF-acid, cyclohexane (about 0.10% of the benzene), light alkylate, detergent alkylate and heavy alkylate. In the soft detergent alkylate process, where the olefinic hydrocarbons are derived from paraffin dehydrogenation, the common practice entails separation of the unreacted paraffins in the alkylation unit rather than in the dehydrogenation unit. Obivously, the recovery of the paraffins is enhanced after the accompanying mono-olefins have been alkylated with the benzene nucleus. However, as a result of these paraffins entering the alkylation process, they will appear in the feed to the fractionation section along with HF-acid, unreacted benzene, cyclohexane, heavy alkylate and detergent alkylate. Fractionation section feed will also contain relatively minor quantities of isoalkylated benzenes, indans and tetralins of the same carbon number range as the linear alkylbenzenes. In both situations, the initial column of the fractionation section is the combination stripping/fractionation vessel hereafter described in greater detail. The principal function of the stripper/fractionator is the recovery of unreacted benzene and HF-acid for subsequent recycle to the reaction section. When producing soft detergent alkylate, the bottoms stream from the stripping/fractionating column in passing into a so-called paraffin column for recovery and recycle of the unreacted paraffins to the dehydrogenation unit. In a detergent alkylation unit which is intended for the alternate production of both hard and soft detergents, the paraffin column is not utilized during the hard operation. Traces of residual hard detergent alkylate, remaining from the hard operation, will appear in the paraffin concentrate during the soft operation and, upon being recycled to the dehydrogenation unit, contaminate the catalytic composite utilized therein. Therefore, in the hard operation, a separation column will be utilized to separate the light alkylate as a side product of the process. In both operations, the mixture of detergent alkylate and heavy alkylate is introduced into an alkylate rerun column, for the recovery of substantially heavy alkylate-free detergent alkylate. The processes will be described in greater detail with reference to the accompanying drawing which illustrates the soft detergent alkylate process incorporating the paraffin column with the alkylate rerun column and the combination stripping/fractionating column.

That part of the reaction section effluent being introduced into the stripping/fractionating column can be broadly characterized as containing benzene (or other unreacted aromatic hydrocarbon), cyclohexane, HF, alkylbenzenes, the alkyl substituent of which contains from about ten to about fifteen carbon atoms per molecule, polyalkyl benzenes and/or polyphenyl alkanes (or other polyaryl alkanes). In virtually every detergent alkylation process, this feed steam will contain both the polyalkyl benzenes and the polyphenyl alkanes. The stripping/fractionating column will function at relatively low pressures in the range of 5 psig. to about 25 psig. -- i.e. a bottoms pressure of about 14 psig. and a top pressure of about 11 psig. Operating temperatures will be from about 150° F. to about 500° F. -- i.e. a top temperature of about 200° F. and a reboiler, or bottoms temperature of about 475° F. At these conditions, with a feed as above described, the stripping/fractionation column provides a bottoms stream containing alkylbenzenes, polyalkyl benzenes and/or polyphenyl alkanes, and the unreacted paraffins from the dehydrogenation unit; this stream is substantially free from benzene and HF-acid, and constitutes the feed to the paraffin column. The overhead stream is substantially a mixture of benzene and HF-acid, and is recycled to the first reaction zone in the reaction section. A contact-condenser is disposed in an upper section of the stripping-fractionating column; that is, in approximately the upper 14.0% of the total length of column. The contact-condenser consists of a lower (about 50.0%) liquid collection zone generally comprising a center-well, and an upper (the remaining 50.0%) packed contacting section. That portion of the overall column which is below the center-well is herein referred to as the "fractionation section", while that portion including the center-well, and above, is referred to as the "stripping", or "contact-condensing" zone.

A principally liquid, benzene-containing side-cut fraction, substantially free from HF, is withdrawn from the center-well. This stream is in a liquid state as a result of the internally disposed contact-condenser immediately above, and thus avoids removing any substantial quantities of HF therewith. The HF entering the contact-condensing section as a vapor continues as such, and is removed in the overhead stream which is recycled to the first reaction zone. The side-cut fraction is utilized within the process in a variety of ways. In the specific illustration hereinafter presented, about 312,564 lbs./hr. of substantially pure benzene (contains about 4.5 mole percent cyclohexane) is withdrawn from the center-well. Of this, 9.89% (by weight) is returned, without substantial temperature change, to the fractionation section above the uppermost tray thereof; 1.38% is introduced, after vaporization, into the acid regenerator to function as the stripping medium; 10.47% is cooled and recycled to first reaction zone; 0.03% is withdrawn from the process as a benzene drag stream to eliminate the possibility of a build-up of cyclohexane; and, 78.23% is cooled and returned to the stripping/fractionating column through a locus above the contact-condenser. The mole ratio of liquid returned to the contact-condenser to the vaporous material passing upwardly into the contact-condenser is in the range of 1.5:1.0 about 6.0:1.0. Principal advantages attendant the use of the combination stripping/-fractionating column, having the internally-disposed contact-condenser include providing a substantially HF-free hydrocarbon stream for the acid regenerator, avoiding excessive cooling and refrigeration duty, otherwise needed to provide a proper column refluxing stream, and the replacement of two columns of currently-practiced processes with a single column. With respect to the latter, the prior art utilized in HF-stripper as a vessel separate from the benzene recovery column.

The bottoms fraction from the stripping/fractionating column constitutes the feed either to the paraffin column, or to the light alkylate column, depending upon the character of the product detergent alkylate -- i.e. whether "soft" or "hard", respectively. The paraffin column will function at temperatures of from 225° F. to about 575° F., typically a bottoms temperature of 500° F. and a top temperature of about 200° F., and at subatmospheric pressure in the range of about 50 to 225mm. Hg., absolute -- i.e. 70 mm. Hg., absolute at the top of the column and 200 mm. Hg., absolute at the top of the column. During the hard detergent alkylate operation, the light alkylate column will function at similar subatmospheric pressures as the paraffin column, but at temperatures of from about 200° F. to about 500° F., typically a top temperature of 215° F. and a bottoms temperature of about 470° F. The operating conditions respecting the alkylate rerun column, whether in the soft, or hard operation, will include temperatures from about 340° F. to about 610° F. -- i.e. a top temperature of about 360° F. and a bottoms temperature of about 590° F., and subatmospheric pressures from about 20 to about 90 mm. Hg., absolute. Preferably, the paraffin column, the light alkylate column and the rerun column will have contact-condensers internally disposed in the upper sections thereof.

Additional description of the present invention will be made with reference to the accompanying drawing which illustrates several embodiments thereof. These are presented by way of a simplified, schematic flow diagram in which details such as compressors, pumps, heaters and coolers, instrumentation and controls, heat-exchange and heat-recovery circuits, valving, start-up lines and similar hardware have either been reduced in number, or eliminated entirely on the grounds of being non-essential to a clear understanding of the techniques involved. The utilization of these miscellaneous appurtenances, to modify the illustrated process, is well within the purview of one skilled in the appropriate art, and the use thereof will not cause a departure from the scope and spirit of the appended claims.

DESCRIPTION OF DRAWING

The drawing will be described in conjunction with a commercially scaled unit designed to produce 30,000 metric tons per year (about 890 Bbl./day), based upon 247 days, of a linear alkylbenzene suitable for ultimate sulfonation to produce soft detergent. The aromatic hydrocarbon is a benzene stream, containing about 4.54 mol.% cyclohexane, in the amount of 467.49 moles/hr. (inclusive of 50.38 moles/hr. of make-up benzene containing about 0.1% of cyclohexane). Normal mono-olefins from a dehydrogenation unit, along with the unreacted paraffins therein, constitute the fresh feed to the first reaction zone.

With particular reference now to the accompanying drawing, the mono-olefinic stream enters the process via line 1, in the amount of about 551.74 moles/hr., and is admixed with 50.38 moles/hr. of a make-up benzene stream from line 2 and 465.74 moles/hr. of a recycled benzene-rich stream from line 3. The recycled benzene stream in line 3 includes 48.18 moles/hr. being returned via line 4 from stripping column 20. Line 4 also contains about 112.40 moles/hr. of HF-acid. The mixture continues through line 3 and is admixed therein with 457.7 moles/hr.of HF from line 5, and 15,799.25 moles/hr. of HF-acid from line 7. The total charge through line 3, into reactor 8, which is maintained at a temperature of about 100° F. and a pressure of 117 psig., consists of 16,369.35 moles/hr. of HF and 1,067.86 moles/hr. of hydrocarbons. A component analysis of the hydrocarbon feed to reactor 8 is presented in the following Table I: Considering only the benzene and the total olefins charged to reactor 8, the mole ratio of benzene/olefin feed is 10.0:1.0.

The total product effluent from the reactor 8 is withdrawn via line 9 and introduced thereby into settler 10,

TABLE I

| Hydrocarbon Feed to Reaction Section | | |
|---|---|---|
| Component | Moles/Hr. | Percent |
| Benzene | 494.90 | 46.35 |
| Cyclohexane | 21.22 | 1.99 |
| N-paraffins, C-11 | 219.04 | 20.51 |
| N-paraffins, C-12 | 159.69 | 14.94 |
| N-paraffins, C-13 | 82.65 | 7.73 |
| N-paraffins, C-14 | 19.17 | 1.80 |
| Cyclo-paraffins | 5.80 | 0.54 |
| Iso-paraffins | 5.04 | 0.47 |
| Aromatics | 10.86 | 1.02 |
| N-olefins, C-11 | 19.12 | 1.80 |
| N-olefins, C-12 | 15.77 | 1.48 |
| N-olefins, C-13 | 9.35 | 0.88 |

TABLE I-continued

| Hydrocarbon Feed to Reaction Section | | |
|---|---|---|
| Component | Moles/Hr. | Percent |
| N-olefins, C-14 | 2.43 | 0.23 |
| Cyclo-olefins | 0.36 | 0.03 |
| Iso-Mono-olefins | 0.44 | 0.04 |
| Di-olefins | 2.02 | 0.19 | wherein the major portion of HF-acid settles into a lower phase, and an upper hydrocarbon phase, containing HF, is removed via line 14. The settled HF phase is withdrawn through line 11 in the amount of 16,382.55 moles/hr.; of this amount, 15,799.25 moles/hr. are diverted through line 7 to be recycled to reactor 8 by way of line 3. The remaining 484.30 moles/hr. continue through line 11 into the upper section of HF-acid regenerator 12. The upper hydrocarbon phase from settler 10, about 1,129.87 moles/hr., is withdrawn through line 14, and introduced thereby into reactor 16 in admixture with 17,379.06 moles/hr. of an HF-rich stream from line 15, containing 457.7 moles/hr. of HF and 55.36 moles/hr. of hydrocarbon from line 6. The total product effluent from reactor 16, at a temperature of 100° F. and a pressure of 65 psig., is introduced, via line 17, into settler 18. The settled HF-acid phase, in an amount of about 17,323.70 moles/hr. is withdrawn through line 5, of which about 16,866 moles/hr. are diverted through line 15 as acid recycle to reaction zone 16. The remaining 457.70 moles/hr. continue through line 5 to be introduced into reactor 8 via line 3. A hydrocarbon/HF phase from settler 18 is withdrawn through line 19, and serves as the feed to the fractionation section of the process. This stream, in the amount of about 138,794 lbs./hr., contains about 1,070.02 moles/hr. of hydrocarbons and 112.40 moles/hr. of HF. The HF-acid phase in line 11, being introduced into acid regenerator 12, is countercurrently contacted therein by a substantially HF-free benzene stream from line 25, in the amount of about 55.36 moles/hr. Acid regenerator 12 functions at a top pressure of about 30 psig., a top temperature of 120° F., a bottoms pressure of 32 psig. and a bottoms temperature of about 350° F. A vaporous stream is withdrawn through line 6, in the amount of 513.06 moles/hr., and is recycled therethrough to reactor 16. A tar bottoms stream, in the amount of 2.09 moles/hr. is withdrawn through line 13.

The feed to the fractionation section (product effluent from the reaction section) through line 19, has the composition, exclusive of HF-acid, presented in the following Table II:

TABLE II

| Reaction Section Hydrocarbon Effluent Analysis | | |
|---|---|---|
| Component | Moles/Hr. | Percent |
| Benzene | 498.12 | 46.55 |
| Cyclohexane | 29.72 | 2.22 |
| N-paraffins, $C_{11}$ | 219.02 | 20.47 |
| N-paraffins, $C_{12}$ | 159.67 | 14.92 |
| N-paraffins, $C_{13}$ | 82.64 | 7.72 |
| N-paraffins, $C_{14}$ | 19.17 | 1.79 |
| Cyclo-paraffins | 5.80 | 0.54 |
| Iso-paraffins | 5.04 | 0.47 |
| Aromatics | 9.17 | 0.86 |
| LAB's, $C_{11}$–$C_{14}$* | 44.18 | 4.13 |
| Iso-alkylated benzenes | 0.40 | 0.04 |
| Indans & Tetralins | 1.26 | 0.12 |
| Heavy Alkylate | 1.82 | 0.17 |

*Linear alkylbenzenes

As hereinbefore stated, my invention may be applied to processes for the production of both soft and hard detergent alkylates. In the illustrative schematic diagram, a soft detergent alkylate process is presented. When converting to the production of hard detergent alkylate, only one reaction zone will be employed, and the paraffin column 32 will not be used; in its stead, a similar column referred to as the "light-alkylate" column will be employed. The latter will, however, be much the same structurally as the illustrated paraffin column.

The reaction section effluent is introduced, via line 19, into stripping column 20 at a locus approximately mid-way with respect to the fractionation section of the column. Fractionation section is herein defined as that lower portion of the column below center-well 22 which contains the distillation trays or decks, and the reboiler section. In a typical operation, where the fractionation section contains 30 trays, the feed will enter just above the fifteenth tray. In the present illustrative embodiment, the operating conditions within stripping column 20 include a top pressure of about 11 psig., a top temperature of about 200° F., a bottoms pressure of about 14 psig. and a bottoms (reboiler) temperature of about 474° F. Its intended function is to provide: a bottoms fraction in line 31 principally comprising the unreacted normal paraffins, the linear alkylbenzenes and the heavy alkylate, and substantially free from benzene and HF-acid; an overhead fraction in line 23 principally comprising benzene and HF, and substantially free from the heavier hydrocarbons; and, a concentrated benzene stream, in line 25, containing at most a trace amount of HF-acid. To accomplish the last two, with any degree of success, in prior detergent alkylate processes required two columns, an HF-stripper and a benzene column. There was necessitated an increase in the number of trays, or decks, of about 66.7%, additional controls, manifolding, separation vessels and other appurtenances, as well as a significant increase in heating and cooling duty (BTU/lb.). In accordance with the present process, column 20 is a combination stripping/fractionation zone having a contact-condenser (liquid countercurrently contacting upwardly flowing vapors) disposed therein about the fractionation section hereinabove defined.

The contact-condenser is hereindefined as that section of the column above the first, or top tray and, includes center-well 22 and contacting zone 21. The vaporous, HF-containing overhead fraction, in the amount of about 6,025 lbs./hr. (160.67 moles/hr.), at a temperature of about 200° F., continues into subcooler 24 wherein the temperature is decreased to about 60° F.; the cooled material is then recycled to the first reaction zone by way of line 4. The substantially HF-free benzene stream (contains a minor quantity of cyclohexane), is withdrawn as a liquid from center-well 22, through line 25, in the amount of about 312,564, lbs./hr.; of this, 30,916 lbs./hr. are reintroduced into the column, at substantially the same temperature, through line 26. The locus of the latter is below center-well 22 and above the first tray of the fractionation section. Of the remaining 281,648 lbs./hr., 4,312 lbs./hr. continue through line 25, and are introduced thereby into acid-regenerator 12 as hereinbefore stated, and 277,336 lbs./hr. are diverted through line 27 into cooler 28. The temperature thereof is lowered from about 195° F. to about 115° F., and the thus-cooled material is withdrawn through line 29. Of this amount, 32,815 lbs./hr. are diverted through line 3, with a drag stream of 86 lbs./hr. being removed from the process via line 30, to prevent a build-up of cyclohexane within the system, and 32,729 lbs./hr. continue through line 3 for recycle to reactor 8.

A portion of the cooled side-cut fraction, 244,521 lbs./hr., continues through line 29, and is re-introduced into stripping column 20 at a locus above contacting zone 21. As previously stated, the mole ratio of the liquid material so introduced into the contact-condenser, to the vapors upwardly flowing thereto from center-well 22, is generally in the range of about 1.5:1.0 to about 6.0:1.0; in the instant situation, this mole ratio approximates 3.03:1.0. Contacting zone 21 can be formed by any suitable material which provides sufficient surface area for effectively contacting the upwardly-flowing vapors. Thus, contacting zone 21 may take the form of a mesh blanket, well known in the art, or an area packed with HF-insensitive balls, rings, saddles, etc.

The bottoms fraction from stripping column 20 continues through line 31, in the amount of 95,642 lbs./hr. (548.17 moles/hr.), and is introduced thereby into paraffin column 32 at a temperature of about 332° F. Paraffin column 22 functions under subatmospheric pressure of about 200 mm. Hg., absolute in the bottoms section, and about 70 mm. Hg. in the upper section, and at a bottoms temperature approximating 500° F. and a top temperature of about 260° F. A bottoms fraction, 11,882 lbs./hr. (47.66 moles/hr.), concentrated in linear alkylbenzenes and heavy alkylate, is withdrawn via line 41. The subatmospheric pressures are instituted by way of line 40 which leads to steam ejectors, or other suitable vacuum jets. Paraffin column 32 has an internally-disposed contact-condenser, comprising center-well 34 and contacting zone 33, disposed above the first tray of the fractionation section. This contact-condenser may take the same shape and form as that described with reference to stripping column 20, although the packing material which forms contacting zone 33 is not required to be HF insensitive. A side-cut fraction, in the amount of about 562,967 lbs./hr. (3,367.07 mole/hr.) is withdrawn from center-well 34, at a temperature of about 240° F., through line 35. At substantially the same temperature, or without intermediate cooling, 91,793 lbs./hr. (549.0 moles/hr.) are diverted via line 36 and introduced into column 32 at a locus below center-well 34 and the top tray of the fractionation section. The remainder continues through line 35, with 387,414 lbs./hr. (2,317.07 moles/hr.) being diverted through line 37. The normal paraffin concentrate, for recycle to the dehydrogenation unit, is removed in the amount of 83,760 lbs./hr. (500.51 moles/hr.). That portion of the side-cut fraction in line 37 is introduced into cooler 38, wherein the temperature is decreased to a level of about 140° F. The thus-cooled material is introduced, via line 39, into column 32 at a locus above contacting zone 32. The mole ratio of the liquid thus countercurrently contacting the upwardly-flowing vapors from the fractionation section is about 2.21:1.0. The normal paraffin stream removed from the process through line 35, is substantially free from linear alkylbenzenes and especially heavy alkylate, and is immediately suitable for return to the dehydrogenation unit.

The bottoms fraction from paraffin column 32, in the amount of 47.66 moles/hr., is introduced, via line 41, into alkylate rerun column 42 at a temperature of about 449° F. through the use of steam ejectors, or vacuum jets, to which line 50 communicates, the rerun column functions at subatmospheric pressures of 25 mm. Hg., absolute at the top, and 85 mm. Hg., absolute at the bottom. The top temperature is about 360° F., and the reboiler, or bottoms temperature of about 590° F. The principal function of the rerun column is to separate the heavy alkylate to the extent that the recovered linear alkylbenzene product is substantially free therefrom -- i.e. less than about 0.01% (mole). This is accomplished by virtue of the fact that the rerun column is also equipped with an internal contact-condenser comprising contacting zone 43 and center-well 44. The heavy alkylate stream is recovered through line 51 in the amount of about 2.23 moles/hr. Since paraffin column 32 and alkylate rerun column 42 function at subatmospheric pressures, the economic advantages of the incorporation of the contact-condensers is even more significant, particularly with respect to the otherwise necessitated external, low pressure-drop condenser.

A liquid stream, in the amount of about 60,020 lbs./hr. (244.88 moles/hr.) is withdrawn from center-well 44 through line 45, and 17,647 lbs./hr. (72.0 moles/hr.) returned to the rerun column via line 46, at a locus below center-well 44 and above the top tray of the fractionation section. Of the remaining 42,373 lbs./hr., entering cooler 47 wherein the temperature is lowered to about 120° F., 11,134 lbs./hr. (45.43 moles/hr.) are removed through line 48 as the produce LAB, while 31,329 lbs./hr. (127.45 moles/hr.) are returned to the column, via line 49, at a locus above contacting zone 43. A component analysis of the recovered linear alkylbenzene product stream is presented in the following Table III:

TABLE III

| Component | Linear Alkylbenzene Product Analysis Moles/Hr. | Percent |
|---|---|---|
| LAB, C-11 | 18.10 | 39.84 |
| LAB, C-12 | 14.93 | 32.86 |
| LAB, C-13 | 8.85 | 19.48 |
| LAB, C-14 | 1.88 | 4.14 |
| Iso-alkylated benzene | 0.40 | 0.88 |
| Indans & Tetralins | 1.24 | 2.73 |
| Heavy Alkylate | 0.03 | 0.07 |

The foregoing demonstrates the process of the present invention and the benefits afforded through the utilization thereof in the production of detergent-grade alkylate.

I claim as my invention:

1. A method for recovering HF and benzene from a mixture thereof with alkylbenzenes, the alkyl group of which contains from ten to about fifteen carbon atoms per molecule, polyalkyl benzenes and/or polyphenyl alkanes, which method comprises the steps of:
   a. introducing said mixture into a combination stripping/fractionating column, at an intermediate first locus thereof;
   b. withdrawing a bottoms fraction from said column, at a lower second locus thereof, containing alkylbenzenes, polyalkyl benzenes and/or polyphenyl alkanes, substantially free from HF and benzene;
   c. withdrawing a side-cut fraction from said column, substantially free from HF, at an intermediate third locus thereof, said third locus being above said first locus and below a contact-condenser disposed in an upper section of said column;

d. introducing a first portion of said side-cut fraction, at substantially the same temperature, into said column, at a fourth locus intermediate said first locus and said third locus;

e. cooling a second portion of said side-cut fraction and introducing said second portion into said column at a fifth locus above said contact-condenser; and, f. withdrawing HF and benzene as an overhead fraction from said column, a sixth locus above said fifth locus.

2. The method of claim 1 further characterized in that said column is maintained at temperatures in the range of about 150° F. to about 500° F. and pressures from 5 psig. to about 25 psig.

3. The method of claim 1 further characterized in that the mole ratio of the second portion of said side-cut fraction, to the vaporous material passing into the contactcondenser from the fractionation section of said column, is in the range of about 1.5:1.0 to about 6.0:1.0.

4. A process for the production of an alkylaromatic hydrocarbon which comprises the steps of:

a. reacting aromatic hydrocarbons with an olefinic hydrocarbon in contact with a hydrogen fluoride catalyst, in a reaction zone at alkylation conditions selected to produce alkylated aromatics;

b. separating the resulting reaction zone effluent, in a separation zone, to provide a hydrocarbon-rich stream, containing hydrogen fluoride, and a hydrogen fluoride-rich stream;

c. introducing at least a portion of said hydrogen fluoride-rich stream into a regeneration zone to produce regenerated hydrogen fluoride and recycling regenerated hydrogen fluoride to said reaction zone;

d. introducing said hydrocarbon-rich stream, containing aromatic hydrocarbons, HF, alkylaromatics, polyalkyl aromatics and/or polyaryl alkanes, into a combination stripping/fractionation zone having a contact-condenser disposed therein, and recovering therefrom (i) an overhead fraction rich in aromatic hydrocarbons and HF, (ii) a bottoms fraction containing alkylaromatics, polyalkyl aromatics and/or polyaryl alkanes and (iii) a side-cut fraction containing aromatic hydrocarbons and substantially free from HF;

e. introducing a first portion of said side-cut fraction, at substantially the same temperature, into said column;

f. introducing a second portion of said side-cut fraction into said regeneration zone and countercurrently contacting therein said hydrogen fluoride-rich stream; and, g. recovering said linear alkylaromatics from said bottoms fraction.

5. The process of claim 4 further characterized in that a third portion of said side-cut fraction is cooled and introduced into said column at a locus above said contact-condenser.

6. The process of claim 4 further characterized in that said alkylation conditions include temperatures in the range of about 0° F. to about 200° F. and pressures in the range of about 15 psig. to about 600 psig.

7. The process of claim 4 further characterized in that said aromatic hydrocarbon is benzene.

8. The process of claim 4 further characterized in that said olefinic hydrocarbon is a normal mono-olefin containing from about ten to about fifteen carbon atoms per molecule.

9. The process of claim 4 further characterized in that said olefinic hydrocarbon is a branched-chain olefin containing from about ten to about fifteen carbon atoms per molecule.

10. A process for producing detergent-grade alkylate which comprises the steps of:

a. reacting aromatic hydrocarbons with an olefinic hydrocarbon in contact with an HF catalyst, in a first reaction zone, at alkylation conditions selected to produce alkylated aromatics;

b. introducing the resulting first reaction zone effluent into a first separation zone to provide a first hydrocarbon phase and a first HF-acid phase;

c. further reacting said first hydrocarbon phase in contact with HF-acid catalyst, in a second reaction zone, at alkylation conditions selected to produce additional alkylated aromatics;

d. recycling a first portion of said first HF-acid phase to said first reaction zone, and introducing a second portion into an upper section of a regeneration zone and countercurrently contacting said second portion therein with an aromatic hydrocarbon-containing stream to provide a regenerated HF-acid phase;

e. recycling at least a portion of said regenerated HF-acid phase to said second reaction zone;

f. introducing the resulting second reaction zone effluent into a second separation zone to provide a second HF-acid phase and a second hydrocarbon phase;

g. recycling at least a portion of said second HF-acid phase to said first reaction zone;

h. introducing said second hydrocarbon phase, containing HF, aromatic hydrocarbons, alkylated aromatics, polyalkyl aromatics and/or polyaryl alkanes into a combination stripping/fractionation zone having a contact-condenser disposed therein, and withdrawing therefrom a side-cut fraction principally containing aromatic hydrocarbons;

i. introducing at least a portion of said sidecut fraction into a lower section of said regeneration zone to countercurrently contact therein the second portion of said HF-acid phase as said aromatic hydrocarbon-containing stream; and, j. recovering said detergent-grade alkylate from the remainder of said second hydrocarbon phase.

* * * * *